(12) United States Patent
Ikeda

(10) Patent No.: US 8,226,991 B2
(45) Date of Patent: Jul. 24, 2012

(54) **FOODSTUFF COMPRISING AN EXTRACT OF A PLANT OF THE GENUS *SALACIA* AND FLAVONOID**

(75) Inventor: Kenji Ikeda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 214 days.

(21) Appl. No.: 12/676,683

(22) PCT Filed: Sep. 3, 2008

(86) PCT No.: PCT/JP2008/066266
§ 371 (c)(1),
(2), (4) Date: Mar. 5, 2010

(87) PCT Pub. No.: WO2009/031690
PCT Pub. Date: Mar. 12, 2009

(65) Prior Publication Data
US 2010/0247501 A1   Sep. 30, 2010

(30) Foreign Application Priority Data

Sep. 6, 2007  (JP) ................ 2007-231909
Sep. 28, 2007  (JP) ................ 2007-256732

(51) Int. Cl.
*A01N 65/00* (2009.01)
(52) U.S. Cl. .................................... 424/725
(58) Field of Classification Search ............ None
See application file for complete search history.

(56) References Cited

U.S. PATENT DOCUMENTS

| 2007/0244202 A1 | 10/2007 | Murase |
| 2011/0319497 A1 | 12/2011 | Murase |

FOREIGN PATENT DOCUMENTS

| JP | 09-301882 A | 11/1997 |
| JP | 3030008 B2 | 2/2000 |
| JP | 2000-086653 A | 3/2000 |
| JP | 2001-524119 A | 11/2001 |
| JP | 3261090 B2 | 12/2001 |
| JP | 2003128571 A | 5/2003 |
| JP | 2003-245057 A | 9/2003 |
| JP | 2003-245095 A | 9/2003 |
| JP | 2003-267881 A | 9/2003 |
| JP | 2004135506 A | 5/2004 |
| JP | 2004-323420 A | 11/2004 |
| JP | 2005-295991 A | 10/2005 |
| JP | 2006020606 A | 1/2006 |
| JP | 2006034265 A | 2/2006 |
| JP | 2006-160710 A | 6/2006 |
| JP | 2006-280236 A | 10/2006 |
| JP | 2007-131620 A | 5/2007 |
| JP | 2007159541 A | 6/2007 |
| WO | 01/76580 A1 | 10/2001 |
| WO | 2006001278 A1 | 1/2006 |

OTHER PUBLICATIONS

Yoshikawa, Masayuki, et al; "*Salacia*"; Food Style 21, May 2005; vol. 6 No. 5; pp. 72-78.
A.M. Hackett; "The disposition of 3-O-methyl-(+)-catechin in the rat and the marmoset following oral administration"; European Journal of Drug Metabolism and Pharmacokinetics; 1983, vol. 8 No. 1; pp. 35-42.
T. Murase, et al.; "Reduction of diet-induced obesity by a combination of tea-catechin intake and regular swimming"; Int'l Journal of Obesity 2006; vol. 30; pp. 561-568.
T. Murase, et al.; "Beneficial effects of tea catechins on diet-induced obesity: stimulation of lipid catabolism in the liver"; Int'l Journal of Obesity 2002; vol. 26; pp. 1459-1464.
Matt Kaeberlein, et al.; "Grapes versus gluttony"; Nature Publishing Group; vol. 444 No. 16; Nov. 2006; pp. 280-281.
Noriyasu Ota, et al.; "Effects of Combination of Regular Exercise and Tea Catechins intake on Energy Expenditure in Humans"; Journal of Health Science 2005; vol. 51 No. 2; pp. 233-236.
Meishiang Jang, et al.; "Cancer Chemopreventative Activity of Resveratrol, a Natural Product Derived from Grapes" Science, AAAS; vol. 275 Jan. 10, 1997; pp. 218-220.
Akria Shimotoyodome, et al.; "Exercise and Green Tea Extract Stimulate Fat Oxidation and Prevent Obesity in Mice"; Medicine & Science in Sports & Exercise; 2005; pp. 1884-1892.
Tsuchida Takashi, et al.; Progress in Medicine 2002; vol. 22 No. 9, pp. 2189-2203.
Hisashi Matsuda, et al.; "Antidiabetogenic constituents from several natural medicines" Pure Appl. Chem. 2002; vol. 74 No. 7; pp. 1301-1308.
Masayuki Yoshikawa, et al.; "Polyphenol Constituents from *Salacia* Species: Quantitative Analysis of Mangiferin with α-Glucidase and Aldose Reductase Inhibitory Activities"; Yakugaku Zasshi 2001; vol. 121 No. 5; pp. 371-378.
Japanese Patent Office, Communication dated Apr. 10, 2012 issued in corresponding Japanese Application No. 2007-256732.

*Primary Examiner* — Michael Meller
(74) *Attorney, Agent, or Firm* — Sughrue Mion, PLLC

(57) ABSTRACT

A foodstuff, includes: an extract of a plant of genus *Salacia*; and a flavonoid, wherein 50% inhibition concentration ($IC_{50}$ value) of sucrase is 300 μg/ml or less.

2 Claims, No Drawings

FOODSTUFF COMPRISING AN EXTRACT OF A PLANT OF THE GENUS *SALACIA* AND FLAVONOID

TECHNICAL FIELD

This invention relates to a foodstuff which comprises an extract of a plant of the genus *Salacia*, wherein 50% inhibition concentration ($IC_{50}$ value) of sucrase is 300 µg/ml or less, and flavonoid.

BACKGROUND ART

Recently, persons having obesity or a little higher blood sugar level caused by the ingestion of high calorie food and overeating or lack of exercise, so-called reserve group of diabetes mellitus, have been increasing. As a prevention of this, supplements aimed at suppressing sugar absorption and fat absorption are on the market. In addition, for the purpose of suppressing high blood sugar level and preventing diabetes mellitus, α-glucosidase inhibitors which suppress formation of glucose from starch and oligosaccharides are also on the market.

For the purpose of preventing obesity, prevention of overeating by controlling ingesting calories and consumption of calories by constant exercise are necessary, but their everyday practice is difficult in reality. In addition, the α-glucosidase inhibitors are effective not only as a therapeutic agent for diabetes mellitus but in dissolving obesity caused by overeating and lack of exercise and diet control. However, these agents (e.g., acarbose (mfd. by Bayer, trade name Gulcobay)), voglibose (mfd. by Takeda Chemical Industries, trade name Basen) and the like) are difficult to obtain, and when these are taken, absorption of polysaccharides into the body can be suppressed but absorption of glucose and the like monosaccharides cannot be suppressed, so that significant sugar absorption-suppressing effect cannot be expected. In addition, problems of various side effects occur sometimes after their taking. Because of this, concern has been directed for the development of a safe and inexpensive natural-origin composition.

As a natural material effective in satisfying such a requirement for obesity and sugar absorption suppression, there are plants of the genus *Salacia*. The root and trunk of a plant of the genus *Salacia* have been used as a natural drug by a traditional medical science, aayurveda, in India and Sri Lanka. It has been handed down in Sri Lanka that the root skin of *Salacia reticulata* is effective in treating rheumatism, gonorrhea and a skin disease and is also used in the treatment of initial stage diabetes mellitus. In India, a root of *Salacia oblonga* is used in similar treatments, and it is said that *Salacia chinensis* is also used in the treatment of diabetes mellitus (FOOD Style 21, vol. 6, no. 5, pp. 72-78).

Thus, it has been handed down that plants of the genus *Salacia* are effective in the prevention and early stage treatment of diabetes mellitus. In recent years, it has been reported that a plant of the genus *Salacia* has the action to suppress increase of blood sugar level, and its action mechanism is the sugar absorption suppressing action based on the α-glucosidase activity inhibition (FOOD Style 21, vol. 6, no. 5, pp. 72-78).

In addition, there are patents on the compounds which are contained in the extraction components of the genus *Salacia* and have the action to inhibit α-glucosidase activity (Japanese Patent No. 3030008, JP-A-2004-323420 and JP-A-2000-86653), and their application examples and patents as anti-diabetic agents based on the α-glucosidase activity inhibitory action (JP-A-9-301882 and Japanese Patent No. 3261090).

Since the sucrase inhibitory activity of most of the supplements on the market which use *Salacia* extract powder is standardized as 250 µg/ml or less, and when their sucrase inhibitory activity is actually measured, it is mostly about 350 µg/ml, so that it is necessary to increase the number of tablets in order to ingest effective amount.

Concern has been directed toward the development of a high concentration *Salacia* extract powder, for the purpose of decreasing the number of tablets by increasing blending amount of Salacia extract powder per tablet.

In addition, it is known that a large quantity of catechins as a kind of polyphenols are contained in the flavonoid-containing tea extract to be used in the invention. Anti-oxidation action, bactericidal action, anticancer action, blood pressure lowering action, blood sugar level suppressing action and the like many physiological actions have been reported on such catechins, and in recent years, effectiveness of the fat combustion for its somatic fat reducing effect has further been reported (Shimotoyodome A., et al., Med. Sci. Sport Exerc., 37, 1884-1892, 2005 and Murase T., et al., Int. J. Obes. Relat. Metab. Disord., 30, 561-568, 2006).

It has been reported that the effect to decrease body weight and somatic fat (abdominal total fat area, visceral fat area) can be seen by the ingestion of high concentration catechin for a prolonged period of time. It is considered that a fat combusting enzyme in cells of the liver is activated by the high concentration catechin and thereby increase energy consumption by activating the fat metabolism, thus resulting in the reduction of somatic fat (Tsuchida T., Itakura H., Nakamura H., Prog. Med., 22, 2189-2203, 2002, Hackett A. M., et al., Eur. J. Drug Metab. Pharmacokinet, 8, 35-42, 1983, Murase T., et al., Int. J. Obes. Relat. Metab. Disord., 26, 1459-1464, 2002 and Ota N., et al., J. Health. Sci., 51, 233-236, 2005).

It is possible to ingest catechin by drinking a green tea or the like tea, but since the content per cup is small, it is necessary to ingest a tea extract powder in the form of tablets or capsules for ingesting a desired amount.

In addition, a tea extract contains catechin, epicatechin, gallocatechin, epigallocatechin, catechin gallate, epicatechin gallate, gallocatechin gallate and epigallocatechin gallate as catechins, or epigallocatechin gallate, epigallocatechin, epicatechin gallate and gallocatechin in order of the content.

In addition, the flavonoid to be used in the invention is roughly divided into flavonols, isoflavones and catechins. Among these, flavonols are a general term of polyphenols, and particularly among them, anti-oxidation action, bactericidal action, anticancer action, immune action, fat combustion and the like many physiological actions have been reported on resveratrol, and further, its effectiveness for fat combustion has been confirmed. Also, effectiveness of the life-prolonging effect of mice which ingested a high calorie feed supplemented with resveratrol has been reported (Science. 275, 218, (1997) and Nature. Nov. 16th. (2006)).

It is possible to ingest resveratrol by drinking or eating a grape extract or drinking red wine or the like, but since the content per once is small, it is necessary to drink a large volume of red wine or ingest it in the form of tablets or capsules for ingesting a desired amount.

In addition, vitamin C absorption support, anti-oxidation action, immune action and the like physiological actions have been reported particularly on quercetin among polyphenols, and it was further confirmed that this is effective in suppressing fat absorption (JP-T-2001-524119 (the term "JP-T" as used herein means a published Japanese translation of a PCT patent application) and WO 01/076580).

It is possible to ingest quercetin by eating an onion, but since the content per once is very small because the skins are not generally used for food. In order to ingest required amount, it is necessary to eat an onion including its skins or ingest its extract powder in the form of tablets or capsules.

Recently, many anti-obesity and after meal blood sugar level increase suppressing foodstuffs have been on the market, and a large number of patents have been applied regarding sugar absorption suppression and fat absorption repression and fat combustion (Japanese Patent No. 3261090, JP-A-2005-295991, JP-A-2006-160710, JP-A-2006-280236 and JP-A-2007-131620). However, very little actually is known about the foodstuff which shows both of the effects on the sugar and fat absorption suppression and the fat combustion by a small amount of ingestion.

DISCLOSURE OF THE INVENTION

Thus, a foodstuff which uses a plant belonging to the genus *Salacia* is possessed of a useful effect such as prevention of diabetes mellitus, but when the sucrase inhibition activity per grain is low ($IC_{50}$ value is large), the necessary ingesting quantity becomes large which is a burden to the ingesting person. Also, it is possible to ingest catechin or resveratrol by drinking green tea or the like tea, drinking or eating a grape extract or drinking red wine or the like, but since the content per once is small, it is necessary to drink a large volume of tea or red wine or ingest it in the form of tablets or capsules for ingesting a desired amount. In addition, it is possible to ingest quercetin in the same manner by eating an onion or drinking its extract powder or the like, but since the content per once is small, it is necessary to eat a large amount of onions or ingest its extract powder in the form of tablets or capsules.

The invention is to provide a foodstuff which shows both of the effects on the sugar and fat absorption suppression and the fat combustion by a small amount of ingestion.

As a result of carrying out intensive studies with the aim of solving the above-mentioned problems, it was found a noteworthy knowledge that when an extract of a plant of the genus *Salacia*, wherein 50% inhibition concentration ($IC_{50}$ value) of sucrase is 300 μg/ml or less, and flavonoid are concomitantly used, sugar absorption is suppressed and fat combustion becomes active by such a small amount of ingestion that obesity and increase of blood sugar level caused by the ingestion of high calorie food and overeating or lack of exercise can be prevented, thereby overcoming the aforementioned technical problems.

That is, the invention is as follows.

(1) A foodstuff, comprising:
an extract of a plant of genus *Salacia*; and
a flavonoid,
wherein 50% inhibition concentration ($IC_{50}$ value) of sucrase is 300 μg/ml or less.

(2) The foodstuff as described in (1) above,
wherein the flavonoid is a substance selected from the group consisting of catechins, flavonols and isoflavones.

(3) The foodstuff as described in (1) or (2) above, comprising:
a tea-derived material containing catechins as a component.

(4) The foodstuff as described in any one of (1) to (3) above, comprising:
at least one species of catechins selected from the group consisting of catechin, epicatechin, gallocatechin, epigallocatechin, catechin gallate, epicatechin gallate, gallocatechin gallate and epigallocatechin gallate.

(5) The foodstuff as described in any one of (1) to (4) above, comprising:
epigallocatechin gallate.

(6) The foodstuff as described in any one of (1) to (5) above, comprising:
from 0.1 to 40% by mass of a tea extract.

(7) The foodstuff as described in any one of (1) to (6) above, comprising:
a grape-derived material containing flavonols as a component.

(8) The foodstuff as described in any one of (1) to (7) above, comprising:
a grape extract or wine concentrate containing flavonols as a component.

(9) The foodstuff as described in any one of (1) to (8) above, comprising:
resveratrol.

(10) The foodstuff as described in any one of (1) to (9) above, comprising:
from 0.1 to 30% by mass of a grape extract.

(11) The foodstuff as described in any one of (1) to (10) above, comprising:
from 0.001 to 5.0% by mass of resveratrol.

(12) The foodstuff as described in any one of (1) to (11) above, comprising:
an onion-derived material containing flavonols as a component.

(13) The foodstuff as described in any one of (1) to (12) above, comprising:
quercetin.

(14) The foodstuff as described in any one of (1) to (13) above, comprising:
from 0.001 to 15% by mass of quercetin.

(15) The foodstuff as described in any one of (1) to (14), further comprising:
from 0.0001 to 0.100% by mass of Chromium yeast, in terms of chromium.

BEST MODE FOR CARRYING OUT THE INVENTION

According to the invention, when tablets or capsules which comprise an extract of a plant of the genus *Salacia*, wherein 50% inhibition concentration ($IC_{50}$ value) of sucrase is 300 μg/ml or less, and a tea extract, are ingested as a foodstuff, its effect can be obtained in such a small amount that the burden to the ingesting person can be alleviated. Also, when tablets or capsules which comprise an extract of a plant of the genus *Salacia* and flavonoid are ingested, not only it becomes possible to prevent obesity and suppress increase in the blood sugar level after meal, but also acceleration of fat metabolism and accumulation of fat are alleviated and, in addition, the effect to improve intestinal environment can also be expected due to their bactericidal action and immune action.

The plant of the invention belonging to the genus *Salacia* is a plant of the family Celastraceae, which grows wild mainly in Sri Lanka and India, and more illustratively, at least one plant selected from *Salacia reticulata, Salacia oblonga, Salacia prinoides* and *Salacia chinensis* is used. Both of its terrestrial parts (leaf, bark, xylem and the like) and subterranean part (root skin) can be used. In the local regions, it is said that the root skin is particularly effective in treating diabetes mellitus, but the activity can be found in the whole plant. The above-mentioned plant of the genus *Salacia* can be used as its dry powder or as an extract from the dry powder, and is generally kept in the form of dry powder of extract therefrom.

According to the invention, the extract of a plant of the genus *Salacia* may be any one of the filtrate after extraction as such, or its concentrated or diluted state or in the form of its dried powder, or a mixture thereof.

The dry extract powder of the aforementioned extract can be used as such when used or by dissolving in an appropriate solvent. The aforementioned solvent may be any substance, with the proviso that it is a solvent which can be used at the time of extraction and does not exert a bad influence upon the human body even when it remained in the drug or foodstuff after preparation, and water, an alcohol or a hydrous alcohol is preferably used. More preferably, hot water or ethanol or hydrous ethanol is used. Regarding the alcohol concentration of the aforementioned hydrous alcohol, those which have a concentration of from 30 to 90% by mass, preferably from 40 to 70% by mass, may be used. As the drying method, spray drying, freeze drying and the like can be exemplified, though not limited thereto.

According to the invention, in order to improve periodical discoloration by the extract powder extracted from the plant of the genus *Salacia*, it is desirable to contain 1% by mass or more of calcium carbonate or silicon dioxide in forming tablets or capsules. Further, a low moisture absorption material or moisture absorbent applicable as a foodstuff or food additive agent can be used. Preferably, cellulose, crystalline cellulose, cellulose powder, microcrystalline cellulose, lactose, an oligosaccharide, a sugar alcohol, trehalose, magnesium stearate, calcium stearate or the like is used as the low moisture absorption material. As the moisture absorbent, silicates, magnesium carbonate, a ferrocyanide, polysaccharides or the like are used. More preferably, crystalline cellulose, microcrystalline cellulose or lactose is used as the low moisture absorption material.

A compound necessary for forming into the powder, solid preparation or liquid preparation of the invention, and the like may be optionally contained. As examples of such a compound, erythritol, maltitol, hydroxypropylcellulose, kaolin, talc and the like can be cited.

According to the invention, conventionally known means and conventionally known materials can be applied to the preparation for obtaining tablets or solutions, granulation of capsule inclusion matter for forming capsules, capsulation, capsule material and the like.

The sucrase 50% inhibitory concentration ($IC_{50}$ value) of the foodstuff of the invention is 300 µg/ml or less. When the inhibition activity becomes smaller than this, the absorption suppressing action of glucose from the digestive tracts becomes weak so that it is necessary to increase the number of ingesting tablets for obtaining the desired effect. The sucrase 50% inhibitory concentration is preferably 250 µg/ml or less, more preferably 200 µg/ml or less.

The sucrase 50% inhibitory concentration ($IC_{50}$ value) is measured by the following method.

[Test method 1] Measurement of sucrase $IC_{50}$ value

Preparation of sample solution: A 2 mg portion of a sample is weighed and put into a tube and thoroughly suspended in 2 ml of water added thereto, thereby preparing a sample solution having a concentration of 1 mg/ml. This is diluted with water to respective concentrations of 0, 50, 100, 250 and 500 µg/ml.

Preparation of substrate liquid: Sucrose is dissolved in 0.2 M maleate buffer (pH 6.0) to a sucrose concentration of 100 mM, and this is used as the substrate liquid.

Preparation of crude enzyme liquid: A 1 g portion of intestinal acetone powder rat (mfd. by SIGMA) is suspended in 10 ml of physiological saline and then centrifuged (3,000 rpm, 4° C., 5 min). The thus obtained supernatant is separated and used as the crude enzyme liquid.

A 400 µl portion of the substrate liquid is added to 500 µl of each of the aforementioned sample solution having respective concentrations and preliminarily heated at 37° C. for 5 minutes in a water bath. A 100 µl portion of the crude enzyme liquid is added to each of them and allowed to undergo the reaction at 37° C. for 60 minutes. After completion of the reaction, the reaction is terminated by deactivating the enzyme through heating at 95° C. for 2 minutes. Determination of concentration of the thus formed glucose is carried out using a commercially available kit for mutarotase glucose oxidase method (Glucose CII Test Wako, mfd. by Wako Pure Chemical Industries).

Preparation of blank: A 200 µl portion of the substrate liquid and 50 µl of the crude enzyme liquid are added to 250 µl of each of the aforementioned sample solution having respective concentrations and immediately heated at 95° C. for 2 minutes to effect thermal deactivation of the enzyme, to be used as blank data.

By preparing a calibration curve from the thus obtained values, the concentration which inhibits 50% of the enzyme activity ($IC_{50}$ value) is calculated.

In this connection, when the sample is in a liquid state, it is used in the above-mentioned Test method 1, by converting it as a powder when its concentration is known, or when unknown, by making it into a powder through its evaporation to dryness. According to the invention, the sucrase $IC_{50}$ value when the sample is in a liquid state means that it is measured on a liquid sample having a 500 µg/ml or more in dry extract powder concentration of an extract of a plant of the genus *Salacia*.

The flavonoid of the invention is a general term for the pigment components distributing in all plant organs, which is contained mainly in fruits and vegetables and is present particularly in the form of glycosides in skins of green and white vegetables and citrus fruits.

According to the invention, the flavonoid is a general term for the pigment components broadly distributing in plants, and particularly, it means flavan derivatives frequently contained in vegetables and fruits.

As the flavonoid, flavonols, isoflavones and catechins are preferable. Flavonols are known as polyphenols.

Flavonoid is a substance ingested into the body, but is generally hard to be absorbed. However, since flavonoid is effective even at a small amount and is a strong antioxidant, it is known that it suppresses the activity of carcinogens and has blood circulation accelerating action and anti-thrombus action.

In the invention, flavonoid can be obtained from tea, grape, onion and the like respective origins. In this case, the origins mean those which are extracted from at least a part of an organism. For example, the above-mentioned method for preparing an extract of a plant of the genus *Salacia* can be employed for the extraction, and the form of the extract can also be the same as described in the above; for example, it may be any one of the filtrate after extraction as such, or its concentrated or diluted state or in the form of its dried powder, or a mixture thereof.

The tea extract containing catechins is prepared from a tea plant which is an evergreen tree belonging to the family Theaceae. As the tea plant, both of the assamica cultivated in India, Sri Lanka and Southeast Asia and *Camellia sinensis* cultivated in China and Japan can be used. In general, water, an alcohol or a hydrous alcohol is preferably used in the extraction. More preferably, hot water or ethanol or hydrous ethanol is used as the extraction solvent. Regarding the alcohol concentration of the aforementioned hydrous alcohol, those which have a concentration of from 30 to 90% by mass, preferably from 40 to 70% by mass, may be used. As the drying method, spray drying, freeze drying and the like can be exemplified, though not limited thereto.

Polyphenol, catechins and the like antioxidants are contained in the tea extract. It is desirable that catechin, epicatechin, gallocatechin, epigallocatechin, catechin gallate, epicatechin gallate, gallocatechin gallate or epigallocatechin gallate is contained therein, it is particularly desirable that epigallocatechin gallate is contained therein.

It is preferable that the foodstuff of the invention contains said tea extract in an amount of from 0.1 to 40% by mass, more preferably from 0.5 to 35% by mass, particularly preferably from 1.0 to 30% by mass. (In this specification, mass ratio is equal to weight ratio.)

Also, the flavonols as one of the flavonoid eliminate active oxygen and thereby show anti-oxidation actions such as suppression of arteriosclerosis and improvement of blood circulation. Among the flavonols, resveratrol as one of the polyphenol has been drawing attention as an antioxidant. Resveratrol is constituted from the stilbene backbone and contained in a large amount in the rind of grapes so that it is also contained in red wine produced from grapes.

It is desirable that the invention comprises a grape extract or grape wine concentrate which contains said flavonols as a component.

It is preferable that the foodstuff of the invention contains the grape extract in an amount of from 0.1 to 30% by mass, more preferably from 0.1 to 10% by mass.

It has been revealed that resveratrol has the actions to burn fat, to prevent a blood vessel system disease, arteriosclerosis, to exert anti-cancer action and to prevent shortening of DNA caused by cell division, and has the effect to prolong life of cells similar to the case of carrying out calorie control, so that it has the excellent effect as a material for preventing life style-related diseases.

The resveratrol content in the foodstuff of the invention is preferably from 0.0001 to 5.00% by mass, more preferably from 0.001 to 2.00% by mass.

In addition, among the flavonols, quercetin as a polyphenol has been drawing attention as an antioxidant. Quercetin has the flavan structure and is contained in a large amount in onion skins.

Vitamin C absorption support, anti-oxidation action, immune action and the like physiological actions of quercetin have been reported, and it has been revealed that it is effective in suppressing fat absorption and it has been revealed also that it has the excellent effect as a material for preventing life style-related diseases.

The quercetin content in the foodstuff of the invention is preferably from 0.001 to 15% by mass, more preferably from 0.05 to 10% by mass, further preferably from 0.1 to 5.0% by mass.

Chromium can be contained in the foodstuff of the invention. Chromium activates the action of insulin which is a hormone that adjusts increase of the blood sugar level, improves metabolism of sugar and suppresses accumulation of fat. In addition, it is known that it prevents diabetes mellitus and normalizes values of neutral fat and cholesterol in blood.

In general, chromium is ingested in the form of Chromium yeast, but it is possible to produce further greater effect by, not ingesting it alone, but using it concomitantly with a material having a sugar absorption suppressing action and fat burning action.

It is preferable that the foodstuff of the invention contains the Chromium yeast in an amount of from 0.0001 to 0.100% by mass, more preferably from 0.001 to 0.050% by mass, further preferably from 0.001 to 0.025% by mass, in terms of chromium.

Embodiment

The following describes the invention based on examples, but the invention is not limited to the following examples.

(Preparation of Extract of Plants of the Genus *Salacia*)

Root and trunk parts of *Salacia reticulata* and *Salacia oblonga* were pulverized and then subjected to a hot water extraction step, and the thus obtained liquid was spray-dried to obtain a *Salacia* extract powder. When the sucrase $IC_{50}$ value was measured using this *Salacia* extract powder by the method described in "Test method 1", it was 78 µg/ml.

(Preparation of Tea Extract)

Leaves of a tea plant produced in Japan were nipped off, dried, pulverized and then subjected to a hot water extraction step, and the thus obtained liquid was spray-dried to obtain a tea extract.

(Preparation of Grape Extract)

Fruit parts of the family Vitaceae were nipped off and, after separating the rind and seeds therefrom, subjected to a hydrous ethanol extraction step, and the thus obtained liquid was spray-dried to obtain a grape-derived product containing resveratrol.

(Preparation Of Onion Skin Extract)

Skin parts of an onion were collected and subjected to a hydrous ethanol extraction step, and the thus obtained liquid was spray-dried to obtain an onion-derived extract powder containing quercetin.

(Inventive Examples 1 to 11 and Comparative Examples 1 to 6)

(Preparation of tablets using *Salacia* Extract Powder and Tea Extract, Grape Extract and Onion Skin Extract)

Tablets 101 to 111 (Inventive Examples) and tablets 112 to 117 (Comparative Examples) were prepared based on the formulations shown in Table 1 and subjected to a shellac coating, thereby preparing respective supplements.

(Discoloration of Tablets after Preservation)

When the tablets prepared in the above were preserved at 30° C. and at 75% humidity for 1 week and discoloration on the tablet surface was examined, Comparative Examples 1, 3 and 6 showed large discoloration, but discoloration was hardly found in other examples.

(Change in Body Weight and Change in Somatic Fat Ratio after Ingestion)

Each of the supplements prepared in the above was ingested 4 tablets per day for 4 weeks, and changes in the body weight, somatic fat ratio and cholesterol value after ingestion were measured. In addition, change in the blood sugar level after meal was also measured.

The results are also shown in Table 1.

TABLE 1

|  | Inv. Ex. 1 | Inv. Ex. 2 | Inv. Ex. 3 | Inv. Ex. 4 | Inv. Ex. 5 | Inv. Ex. 6 | Inv. Ex. 7 | Inv. Ex. 8 | Inv. Ex. 9 |
|---|---|---|---|---|---|---|---|---|---|
| Material name/mixing amount (% by mass) | Tablet 101 | Tablet 102 | Tablet 103 | Tablet 104 | Tablet 105 | Tablet 106 | Tablet 107 | Tablet 108 | Tablet 109 |
| *Salacia* extract powder | 25 | 25 | 25 | 25 | 25 | 25 | 25 | 25 | 25 |
| Red wine polyphenol | 10 | 10 | 10 | 10 | 10 | 7.5 | 0 | 0 | 10 |
| Onion skin extract powder | 6 | 6 | 6 | 6 | 0 | 6 | 6 | 0 | 0 |

TABLE 1-continued

| Material | | | | | | | | | |
|---|---|---|---|---|---|---|---|---|---|
| Tea extract | 15 | 15 | 15 | 0 | 15 | 0 | 15 | 15 | 0 |
| *Haematococcus algal* pigment | 1 | 1 | 1 | 1 | 1 | 1 | 1 | 1 | 1 |
| Chromium yeast | 0 | 4 | 4 | 0 | 4 | 0 | 4 | 4 | 4 |
| Carnitine | 10 | 10 | 10 | 10 | 10 | 10 | 10 | 10 | 10 |
| Crystalline cellulose | 27 | 29 | 23 | 42 | 29 | 44.5 | 33 | 39 | 44 |
| Sucrose fatty acid ester | 2 | 2 | 2 | 2 | 2 | 2 | 2 | 2 | 2 |
| Lactose | 1 | 1 | 1 | 1 | 1 | 1 | 1 | 1 | 1 |
| Calcium carbonate | 1 | 1 | 1 | 1 | 1 | 1 | 1 | 1 | 1 |
| Fine grain silicon dioxide | 2 | 2 | 2 | 2 | 2 | 2 | 2 | 2 | 2 |
| Measuring items | | | | | | | | | |
| Change in body weight | – | – – | – | – | – – | – | – – | – – | – – |
| Change in somatic fat ratio | – | – – | – | – | – | – | – | – – | – |
| Blood sugar level after meal | – – | – – | – | – – | – – | – | – – | – | – – |
| Cholesterol value | – | – – | – | – | – – | ± | – | – – | – |

| | Inv. Ex. 10 | Inv. Ex. 11 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| Material name/mixing amount (% by mass) | Tablet 110 | Tablet 111 | Tablet 112 | Tablet 113 | Tablet 114 | Tablet 115 | Tablet 116 | Tablet 117 |
| *Salacia* extract powder | 25 | 25 | 25 | 25 | 25 | 25 | 25 | 25 |
| Red wine polyphenol | 0 | 7.5 | 0 | 0 | 0 | 0 | 0 | 0 |
| Onion skin extract powder | 6 | 6 | 0 | 0 | 0 | 0 | 0 | 0 |
| Tea extract | 0 | 15 | 0 | 0 | 0 | 0 | 0 | 0 |
| *Haematococcus algal* pigment | 1 | 1 | 1 | 1 | 1 | 1 | 1 | 1 |
| Chromium yeast | 4 | 0 | 0 | 0 | 4 | 0 | 0 | 4 |
| Carnitine | 10 | 10 | 10 | 10 | 10 | 10 | 10 | 10 |
| Crystalline cellulose | 48 | 39.5 | 61 | 58 | 59 | 52 | 27 | 36 |
| Sucrose fatty acid ester | 2 | 2 | 2 | 2 | 0 | 2 | 2 | 0 |
| Lactose | 1 | 1 | 1 | 1 | 1 | 1 | 1 | 1 |
| Calcium carbonate | 1 | 1 | 0 | 1 | 0 | 1 | 1 | 0 |
| Fine grain silicon dioxide | 2 | 2 | 0 | 2 | 0 | 2 | 2 | 0 |
| Measuring items | | | | | | | | |
| Change in body weight | – | – | + | + | ± | + | + | ± |
| Change in somatic fat ratio | – | – | + | + | + | + | + | + |
| Blood sugar level after meal | – | – | – | – | ± | – | – | ± |
| Cholesterol value | ± | ± | + | + | ± | + | ± | ± |

Note)
Increase before and after ingestion: ++, slight increase: +, no change: ±, slight decrease: –, decrease: – –
Inv. Ex.: Inventive Example, Comp. Ex.: Comparative Example It can be seen that the foodstuff of the invention is effective for the suppression of obesity, after meal blood sugar level increase and fat.

INDUSTRIAL APPLICABILITY

The invention contemplates realizing efficient sugar absorption suppression and fat combustion with such a small amount of ingestion that it does not becomes a burden to the digesting person, effected by a foodstuff in the form of tablets or capsules which comprises an extract of a plant of the genus *Salacia*, wherein 50% inhibition concentration (IC$_{50}$ value) of sucrase is 300 μg/ml or less, and flavonoid.

The entire disclosure of each and every foreign patent application from which the benefit of foreign priority has been claimed in the present application is incorporated herein by reference, as if fully set forth.

The invention claimed is:

1. A foodstuff for suppressing sugar and fat absorption in a patient consisting essentially of therapeutically effective amounts of *salacia reticulata* extract, tea extract, grape extract, onion extract, and chromium yeast.

2. A foodstuff for suppressing sugar and fat absorption in a patient consisting essentially of therapeutically effective amounts of *salacia oblonga* extract, tea extract, grape extract, onion extract, and chromium yeast.

* * * * *